United States Patent
Yee

(10) Patent No.: US 11,419,582 B2
(45) Date of Patent: Aug. 23, 2022

(54) ULTRASOUND IMAGING SYSTEM WITH A MULTI-MODE TOUCH SCREEN INTERFACE

(71) Applicant: KONINKLIJKE PHILIPS N.V., Eindhoven (NL)

(72) Inventor: Wendy Mei Yee, Bothell, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 347 days.

(21) Appl. No.: 16/065,904

(22) PCT Filed: Dec. 28, 2016

(86) PCT No.: PCT/EP2016/082790
§ 371 (c)(1),
(2) Date: Jun. 25, 2018

(87) PCT Pub. No.: WO2017/114874
PCT Pub. Date: Jul. 6, 2017

(65) Prior Publication Data
US 2020/0281565 A1 Sep. 10, 2020

Related U.S. Application Data

(60) Provisional application No. 62/272,114, filed on Dec. 29, 2015.

(51) Int. Cl.
*A61B 8/00* (2006.01)
*G06F 3/044* (2006.01)
(Continued)

(52) U.S. Cl.
CPC ............ *A61B 8/467* (2013.01); *A61B 8/4427* (2013.01); *A61B 8/54* (2013.01); *G06F 3/044* (2013.01); *G06F 3/0487* (2013.01); *G06F 3/14* (2013.01)

(58) Field of Classification Search
CPC ......... A61B 8/467; A61B 8/4427; A61B 8/54; G06F 3/044; G06F 3/0487; G06F 3/14; G06F 1/1692
(Continued)

(56) References Cited

U.S. PATENT DOCUMENTS 5,924,988 A 7/1999 Burris et al.
6,440,072 B1* 8/2002 Schuman ............. A61B 5/0017
600/437
(Continued)

FOREIGN PATENT DOCUMENTS

CN 202776368 U 3/2013
JP 2009153917 A 7/2009
JP 2014117360 A 6/2014

OTHER PUBLICATIONS

Asus Taichi: "Ultrabook, Office Home and Business"; Article on ASUSTek Computer, Feb. 19, 2014, 4 Page Document.

*Primary Examiner* — Alexander Eisen
*Assistant Examiner* — Nathaniel P Brittingham

(57) ABSTRACT

The present disclosure describes ultrasound imaging systems and methods for operating an ultrasound system with a multi-mode touch screen interface. An ultrasound system according to the present disclosure may include a movable base and a control panel supported by the movable base. The control panel may include a plurality of manual controls provided on a support surface and a touch control panel movably coupled to the support surface. The touch control panel may include a touch display configured to provide a touch-sensitive user interface. The touch control panel may be movable between a plurality of positions at which the touch display is at different angles relative to the support surface. The touch display may be configured to automati-
(Continued)

cally change a user interface provided on the touch display responsive to movement of the touch display to any of the plurality of positions.

16 Claims, 9 Drawing Sheets

(51) Int. Cl.
 *G06F 3/0487* (2013.01)
 *G06F 3/14* (2006.01)
(58) Field of Classification Search
 USPC .................................................... 348/14.07
 See application file for complete search history.

(56) References Cited

U.S. PATENT DOCUMENTS

| | | | |
|---|---|---|---|
| 6,443,896 B1 | 9/2002 | Detmer | |
| 6,530,885 B1 | 3/2003 | Entrekin et al. | |
| 7,136,282 B1* | 11/2006 | Rebeske | G06F 1/1616 |
| | | | 361/679.55 |
| 8,480,214 B2 | 7/2013 | Tsubaki | |
| 9,848,849 B2 | 12/2017 | Scott et al. | |
| 2003/0112588 A1* | 6/2003 | Shimano | G06F 1/1679 |
| | | | 361/679.06 |
| 2006/0045495 A1 | 3/2006 | Prabhune et al. | |
| 2008/0119731 A1 | 5/2008 | Becerra et al. | |
| 2008/0146922 A1 | 6/2008 | Steins et al. | |
| 2008/0234577 A1* | 9/2008 | Murkowski | A61B 8/00 |
| | | | 600/437 |
| 2010/0303544 A1 | 12/2010 | Fujii et al. | |
| 2010/0305444 A1 | 12/2010 | Fujii et al. | |
| 2010/0315481 A1* | 12/2010 | Wijngaarden | H04N 7/142 |
| | | | 348/14.07 |
| 2012/0327225 A1* | 12/2012 | Barley | H04N 7/188 |
| | | | 348/143 |
| 2014/0221835 A1 | 8/2014 | Ota | |
| 2014/0292697 A1 | 10/2014 | Morishita | |
| 2014/0365919 A1* | 12/2014 | Shaw | H04M 1/72522 |
| | | | 715/753 |
| 2014/0378833 A1 | 12/2014 | Chen et al. | |
| 2015/0022442 A1* | 1/2015 | Hwang | G06F 1/1618 |
| | | | 345/156 |
| 2015/0150521 A2 | 6/2015 | Roncalez et al. | |
| 2016/0120507 A1 | 5/2016 | Nimomiya et al. | |
| 2016/0274722 A1 | 9/2016 | Putzolu et al. | |
| 2017/0131118 A1* | 5/2017 | Kauhaniemi | G01D 5/145 |

* cited by examiner

| Example: Touch screen content for elevated vs. lowered touch screen positions | OB Ultrasound Application | CV Ultrasound Application |
|---|---|---|
| | Preset: OB Gen | Preset: TEE Interventional |
| Elevated Touch screen | 2D Imaging, Frozen | |
| Elevated Touch screen | OB Analysis Tool | CV 2D Frozen & Cine controls |
| Lowered Touch screen | QWERTY Touch screen | CV Findings selection |
| | 3D/4D Imaging, Live Volume | |
| Elevated Touch screen | OB 3D controls | CV 3D controls |
| Lowered Touch screen | OB Rendering tools, light source manipulation | Mitral valve visualization and cropping tools |

FIG. 6

ULTRASOUND IMAGING SYSTEM WITH A MULTI-MODE TOUCH SCREEN INTERFACE

This application is the U.S. National Phase application under 35 U.S.C. § 371 of International Application No. PCT/EP2016/082790 filed on Dec. 28, 2016, which claims the benefit of Provisional Application Ser. No. 62/272,114, filed Dec. 29, 2015. These applications are hereby incorporated by reference herein.

BACKGROUND

The present disclosure relates generally to medical imaging systems such as ultrasound imaging systems. Ultrasound imaging systems, such as cart-based ultrasound systems, typically include a user interface which operates in conjunction with a display to provide medical images from signals transmitted and received via a transducer probe. Often the user interface includes one or more manual controls. In addition, ultrasound imaging systems frequently include touch screens as a way of displaying secondary menus and controls to the clinician during a patient exam. Such touch screens may be configurable per application. However, touch screens in commercially available systems may have shortcomings in particular relating to ergonomics and usability. In additions, clinicians may require additional flexibility in the ultrasound menus available to them. Improvements of the user interface of ultrasound systems may thus be desirable.

SUMMARY OF THE INVENTION

An ultrasound imaging system according to the present disclosure may include a movable base and a control panel supported by the movable base. The control panel may include a plurality of manual controls provided on a support surface and a touch control panel movably coupled to the support surface. The touch control panel may include a touch display configured to provide a touch-sensitive user interface. The touch control panel may be movable between a plurality of positions at which the touch display is at different angles relative to the support surface. The touch display may be configured to automatically change a user interface provided on the touch display responsive to movement of the touch display to any of the plurality of positions.

An ultrasound imaging system according to further examples herein may include a movable base and a control panel supported by the movable base. The control panel may include a support surface and a touch control panel movably coupled to the support surface. The touch control panel may include a first touch display on a first side of the touch control panel and a second touch display on a second side of the touch control panel opposite the first side. The touch control panel may be pivotable between a first position at which the touch control panel is at a first angle relative to the support surface and a second position in which the touch control panel is at a second angle relative to the support surface smaller than the first angle, the first and second touch displays configured to provide respective first and second user interfaces responsive to pivoting of the touch control panel to the first and second position, respectively. In some examples, the first position may correspond to an elevated position in which the first touch display is accessible and the second position may correspond to a lowered position in which the second touch display is accessible. In some examples, the first touch display may be inaccessible in the lowered position. The ultrasound imaging system may further include a transducer probe removably coupled to the base.

A method of operating an ultrasound imaging system according to some examples herein may include displaying a first default user interface on a touch display of an ultrasound imaging system when the touch display is in a first position relative to a manual control panel of the ultrasound imaging system, wherein the first default user interface includes one or more touch-sensitive areas on the touch display associated with a first mode of operation. The method may further include moving the touch display to a second position relative to the manual control panel and automatically displaying a second default user interface on the touch display responsive to the moving the touch display to the second position, the second default user interface associated with a second mode of operation different from the first mode.

BRIEF DESCRIPTION OF THE DRAWINGS

FIG. 6 is a table illustrating examples of user-configurable settings for ultrasound systems in accordance with the present disclosure.

DETAILED DESCRIPTION OF PREFERRED EMBODIMENTS

Figure 1:
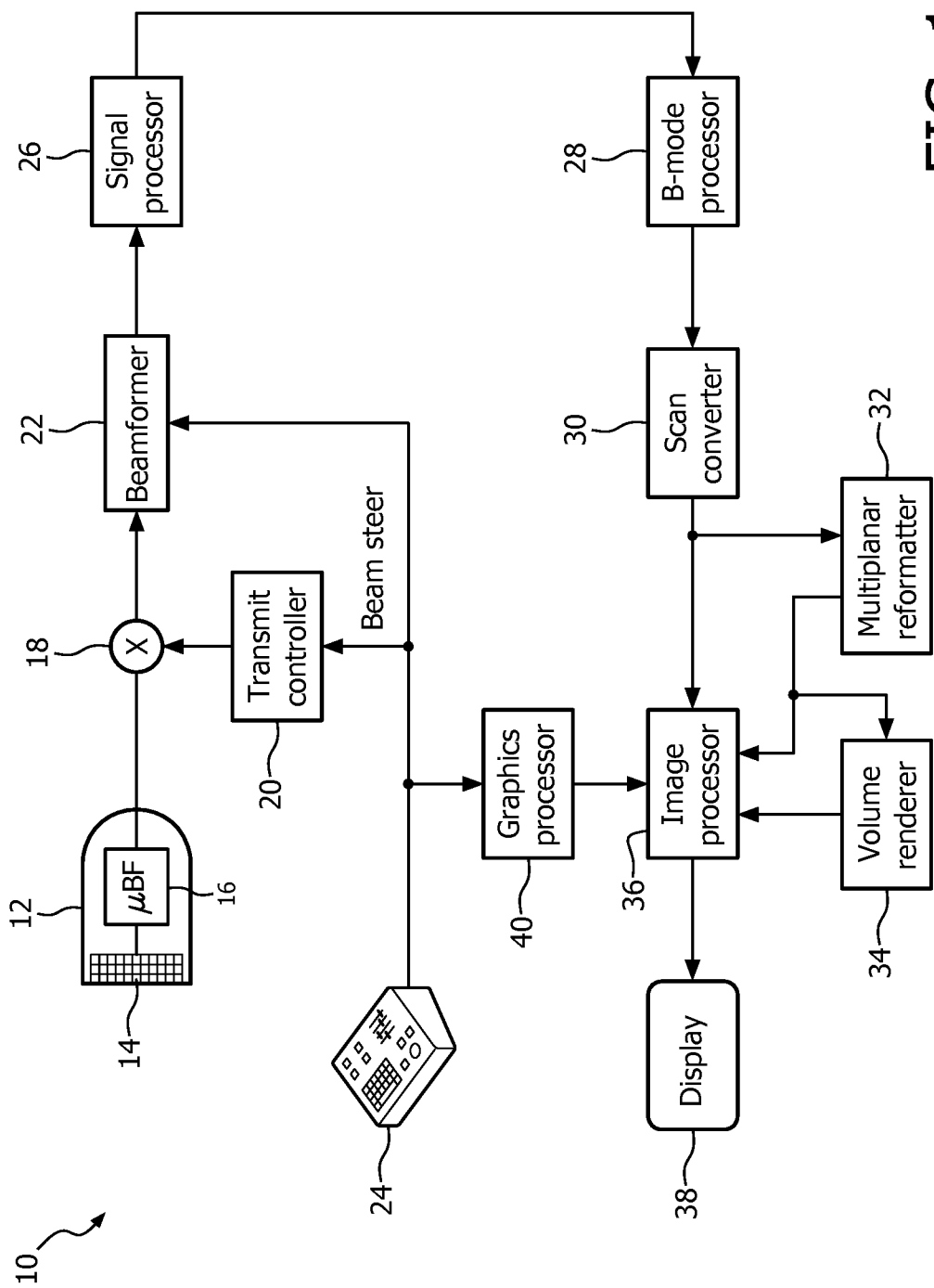
FIG. 1 is a block diagram of an imaging system according to embodiments of the present disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

In one embodiment there is provided a medical imaging system (e.g., an ultrasound imaging system system) with a multi-mode touch screen interface. Methods for operating an ultrasound imaging system which include such multi-mode touch screen interfaces may improve the ergonomics and usability of the imagining system. As noted above, ultrasound imaging systems frequently include touch-sensitive displays (also referred to as touch displays or touch screens) as a way of displaying secondary menus and controls to the clinician. Such touch screens may have the benefit of providing a user interface which is configurable per application (e.g., for a particular clinical use of the system, such as cardiovascular, obstetrical, or others). However, the usability and ergonomics of touch screens which are positioned, for example, in an elevated (e.g., inclined position) may be suboptimal for the clinical user during some operations. At such elevated (e.g., inclined) position, the touch screen may be farther away from the user which may require the user to operate the touch screen with extended arm(s) and/or awkwardly angled wrists. Thus, during some operations, such as typing, it may be ergonomically preferable to position the touch screen at a lowered position (e.g., generally horizontal or slightly downwardly inclined) and/or a position which places the touch screen closer to the user as compared to the elevated position typical for touch screens of commercially available ultrasound systems. One solution may be to include multiple touch-sensitive displays at pre-determined locations, each pre-configured to perform specific functions or present a preset user interface. However, such configuration would increase the size of the system, which may be undesirable particularly for movable (e.g., cart-based) ultrasound systems. The present disclosure describes a compact solution in which an ultrasound imaging system is provided with a multi-mode touch screen interface. The touch screen interface may be provided on one or more touch-sensitive display which may be movable between two or more preferred positions. The multi-mode touch screen interface may be configured to display a different user-configurable default user interface at each of the preferred positions, which may enable the user to switch between operations seamlessly and with minimal effort. In addition, by providing a plurality of default user interfaces, the user may not need to interrupt a workflow that has been initiated on a first touch display to access additional functions. The user may be able to switch to another function via the second or additional user interfaces without having to end the first workflow, which may provide significant increase in efficiency.

As noted, multi-mode touch screen interfaces according to the present disclosure may be implemented using a single touch display or a plurality of touch displays as will be further described. The panel may be moved or articulated in a manner to allow given one of the touch displays to be positioned in a first elevated position and the same or another one of the touch displays to be positioned in a second lowered position. In the lowered position, the touch display may provide greater ergonomic access and reduce or minimize the reach from user. According to some examples, the ultrasound imaging system includes a first and second touch display provided on opposite sides of a single touch control panel. The panel is movable (e.g., pivotable) to change the display that's presented to the user of the ultrasound system. The terms user, clinical user, or operator may be used interchangeably throughout. In some examples, a single touch display may be movably (e.g., slidably) connected to the support structure to enable the touch display to be articulated between the preferred positions and may thereby improve the ergonomics of the systems. In some examples, the one or more movable touch displays may be provided alone or in addition to manual controls (e.g., trackball, keys, switches, buttons, etc.) of the ultrasound system. In some examples, manual controls may be provided on the transducer probe and a movable touch display may be provided on the cart.

FIG. 1 shows block diagram of an ultrasound imaging system 10 constructed in accordance with the principles of the present invention. Although an ultrasound imaging system is shown in explanatory examples of embodiments of the invention, embodiments of the invention may be practiced with other medical imaging modalities. Other modalities may include, but are not limited to, magnetic resonance imaging and computed tomography. The ultrasound imaging system 10 in FIG. 1 includes an ultrasound probe 12 which includes a transducer array 14 for transmitting ultrasonic waves and receiving echo information. A variety of transducer arrays are well known in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. The transducer array 14 is coupled to a microbeamformer 16 in the ultrasound probe 12 which controls transmission and reception of signals by the transducer elements in the array. In this example, the microbeamformer 16 is coupled by the probe cable to a transmit/receive (T/R) switch 18, which switches between transmission and reception and protects the main beamformer 22 from high energy transmit signals. In some embodiments, for example in portable ultrasound systems, the T/R switch 18 and other elements in the system can be included in the ultrasound probe rather than in a separate ultrasound system base. The transmission of ultrasonic beams from the transducer array 14 under control of the microbeamformer 16 is directed by the transmit controller 20 coupled to the T/R switch 18 and the beamformer 22, which receive input from the user's operation of the user interface or control panel 24. One of the functions controlled by the transmit controller 20 is the direction in which beams are steered. Beams may be steered straight ahead from (orthogonal to) the transducer array, or at different angles for a wider field of view. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B-mode processor 28, which can employ amplitude detection for the imaging of structures in the body. The signals produced by the B-mode processor 28 are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D)

sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.) The 2D or 3D images are coupled from the scan converter 30, multiplanar reformatter 32, and volume renderer 34 to an image processor 36 for further enhancement, buffering and temporary storage for display on an image display 38. The graphics processor 40 can generate graphic overlays for display with the ultrasound images. These graphic overlays can contain, e.g., standard identifying information such as patient name, date and time of the image, imaging parameters, and the like. For these purposes the graphics processor receives input from the user interface 24, such as a typed patient name. The user interface can also be coupled to the multiplanar reformatter 32 for selection and control of a display of multiple multiplanar reformatted (MPR) images.

Figure 2:
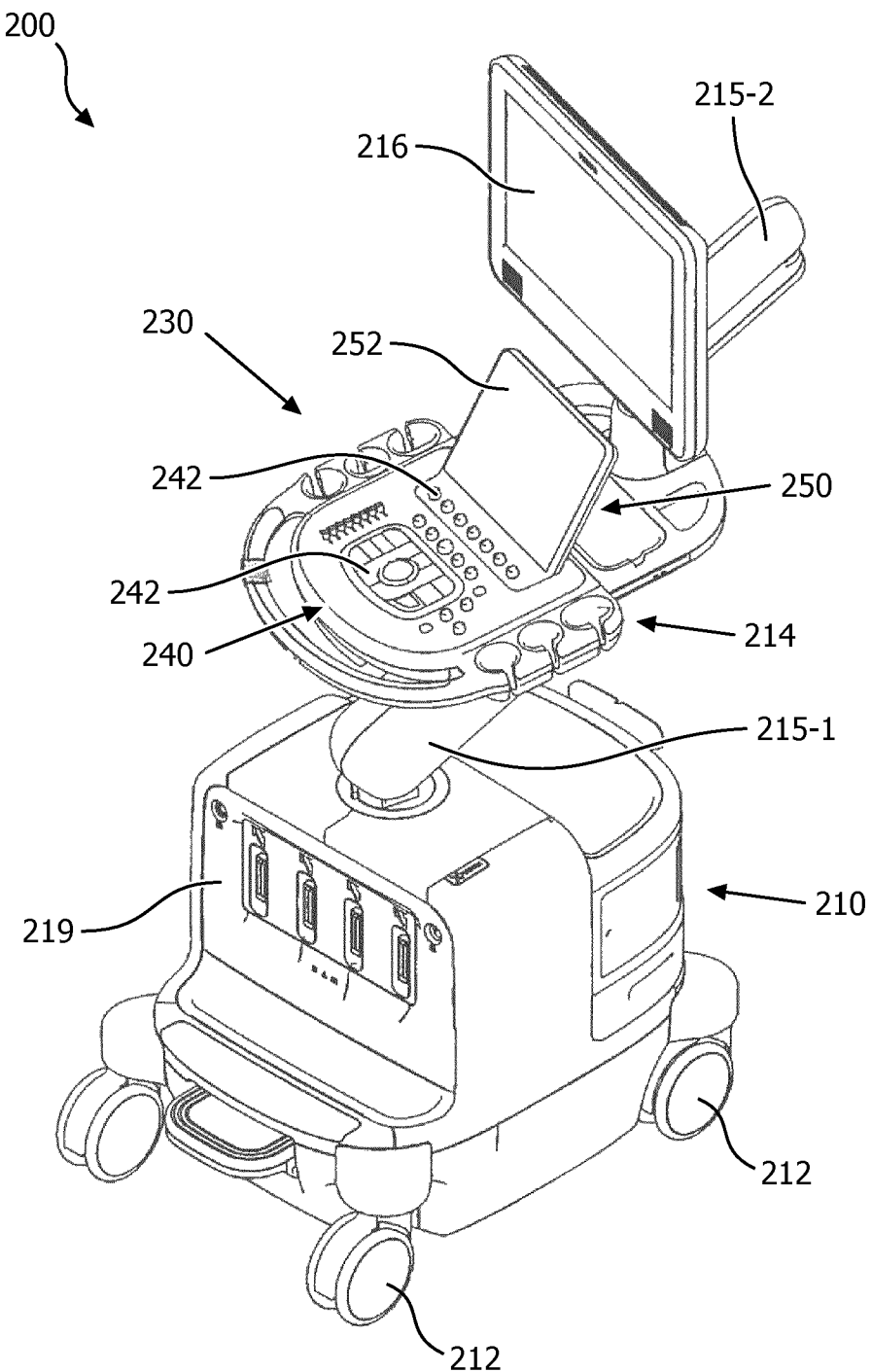
FIG. 2 is a view of an ultrasound imaging system which may include a multi-mode touch screen interface according to examples of the present disclosure.

FIG. 2 illustrates an ultrasound imaging system 200 which may include a multi-mode touch screen interface in accordance with principles of the present invention. The ultrasound imaging system 200 may include some or all of the components of imaging system 10 described with reference to FIG. 1, for example one or more processors such as a signal processor, a B-mode processor, an image processor, and/or a graphics processor. The functionality of these processors, as well as additional functionality of the system 200 may be incorporated into a single processing unit or may be implemented in one or more separate processing units. The imaging system 200 may be a cart-based system, e.g., as illustrated in the example in FIG. 2. To that end, the ultrasound imaging system may include a base 210 (e.g., a cart). The base may be a movable base which includes casters or wheels 212 that facilitate movement of the ultrasound imaging system from one location to another, such as between patient and exam rooms, labs, or surgical rooms. One or more of the electronic components of the ultrasound system, such as one or more processors, controllers, signal generators/receivers, and/or input and output (I/O) devices 219 may be provided in the base 210. One or more ultrasound transducer probes (not shown) may be coupled to the base 210. In some examples, the ultrasound probes may be removably coupled to the base 210.

The system 200 may include a control platform 214 which supports a control panel 230. The control platform 214 may be adjustably connected to the base 210, e.g., via an articulating arm 215-1. The control panel 230 may include a manual control panel 240 and a touch control panel 250. The manual control panel 240 may include a plurality of manual controls 242, such as one or more dials, buttons, knobs, switches, keyboards, trackballs, or the like. The manual controls 242 may be implemented as any of a variety of physical or mechanical input devices which provide tactile feel or feedback to the operator when controlling the system 200 via the manual controls. The touch control panel 250 may include one or more touch displays 252, which may be movable relative to the manual control panel 240 as will be further described. In this manner, the control panel may provide a touch screen interface, which may be user-configurable in some examples. Despite the proliferation and versatility of touch sensitive controls, manual controls may still be desirable because manual controls provide a tactile feedback which may enable the operator to perform certain functions without having to look at the controls. However, examples that include only a touch screen interface are also envisioned and within the scope of this disclosure. In some examples, one or more manual controls may, alternatively or additionally, be provided on the transducer probe. In some examples, only a touch screen interface may be provided on the base of the ultrasound system.

In some examples, the control panel 230, or a portion thereof, may be irremovably attached to (i.e. integrated into) the control platform 214. For example, the manual control panel 240 may be integrated into the control platform 220. In other examples, the control panel 230, or a portion thereof, as well as certain functionality of the ultrasound system may be incorporated into a portable unit (e.g., portable unit 333 in FIG. 3), which may be separable from the base 210. In such examples, the ultrasound system 200 may include a docking structure (not shown), provided on or proximate the control platform 214 to allow the portable unit to be removably attached and operatively (e.g., electrically) coupled to the base 210. In some examples, the system 200 may include an additional display or monitor 216 separate from the touch display 252. The monitor 216 may be adjustably connected to the base 210 and/or control platform 220, for example via an articulating arm 215-2. In some examples, the monitor 216 may be a passive display (e.g., may not include touch-sensitive portions) and may be used to display images acquired with the ultrasound system 200 or another imaging system. In some examples, images, graphic overlays including patient information or relevant clinical measurements or other data displayed on any of the touch displays 252 of the ultrasound system 200 may be replicated on the monitor 216.

Figure 3:
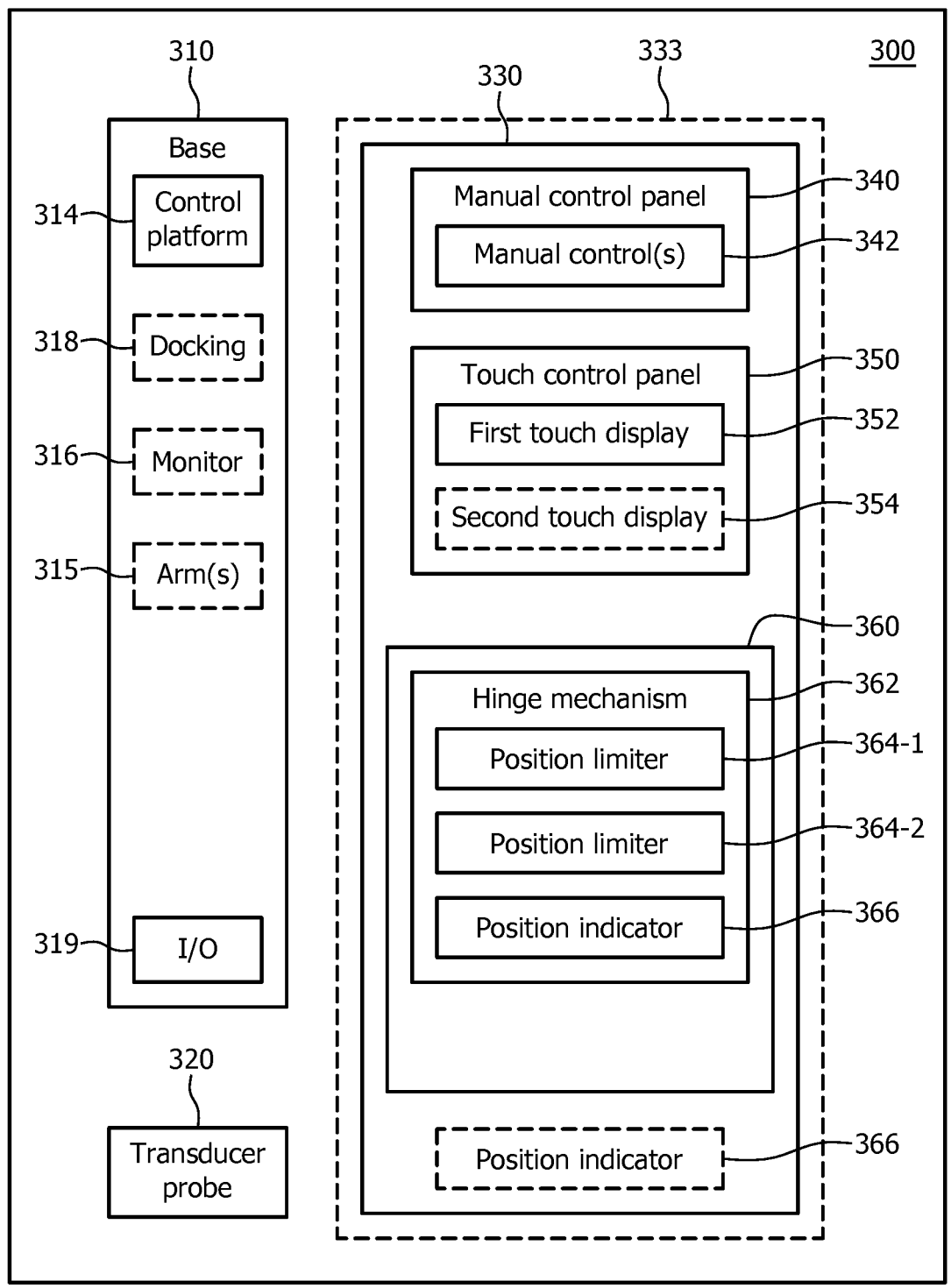
FIG. 3 is a block diagram of an imaging system according to further examples of the present disclosure.

FIG. 3 shows a block diagram of an ultrasound system 300 according to examples of the present disclosure. The ultrasound system 300 may include some or all of the components of ultrasound systems 10 and 200 described previously and for brevity their description will not be repeated. Similar components may be designated using similar numbers with the first numeral corresponding to the respective figure number. For example, the ultrasound system 300 may include a user interface or control panel 330, which may include a multi-mode touch interface in accordance with the present invention. The control panel 330 may include a touch control panel 350 with at least one touch display. The touch display may be movably connected to the supporting structure such that the touch display is movable between a first position and a second position. The control panel 330 may also include a plurality of manual controls 342 (e.g., knobs, trackballs, or the like) provided on a manual control panel 340.

The touch display may be movable between at least a first position, such as an elevated position, and a second position, such as a lowered position. The elevated position may be an inclined position in which the touch display is angled with respect to a support surface (e.g., the upper surface of the control platform 314). The lowered position may be a position in which the touch display is generally parallel with the support surface. In some examples, the support surface may be generally horizontal or slightly downwardly inclined relative to the ground, thus the touch display may be movable to a position in which the touch display is generally horizontal or slightly downwardly inclined with respect to the ground. Such configuration may provide an improved ergonomic position for a touch screen interface during some operations, such as typing. In some examples, a single movable touch display may be used and the touch display may be articulated between the two or more preferred positions to provide the touch display in a horizontal or angled orientation. In some examples, e.g., as described further with reference to FIGS. 4 and 5, the touch control panel 350 includes a plurality of touch displays (e.g., first touch display 352 and second touch display 354).

The touch control panel 350 may be coupled to the support structure (e.g., base 310) via an attachment mechanism 360 configured to enable movement of the touch control panel 350 relative to the support structure. In some examples, the attachment mechanism 360 may provide a pivotable attachment of the touch control panel 350 to the base. For example, the touch control panel 350 may be pivotably coupled via a hinge mechanism 360. In this manner, the touch control panel 350 may thus be articulated to access the first or second touch displays 352, 354. In other examples, the attachment mechanism may provide a slidable attachment of the touch control panel, e.g., via a rail allowing the touch control panel to slide between the horizontal and angled orientation. Other techniques for attaching the touch control panel in a movable manner may be used.

Figure 4A:
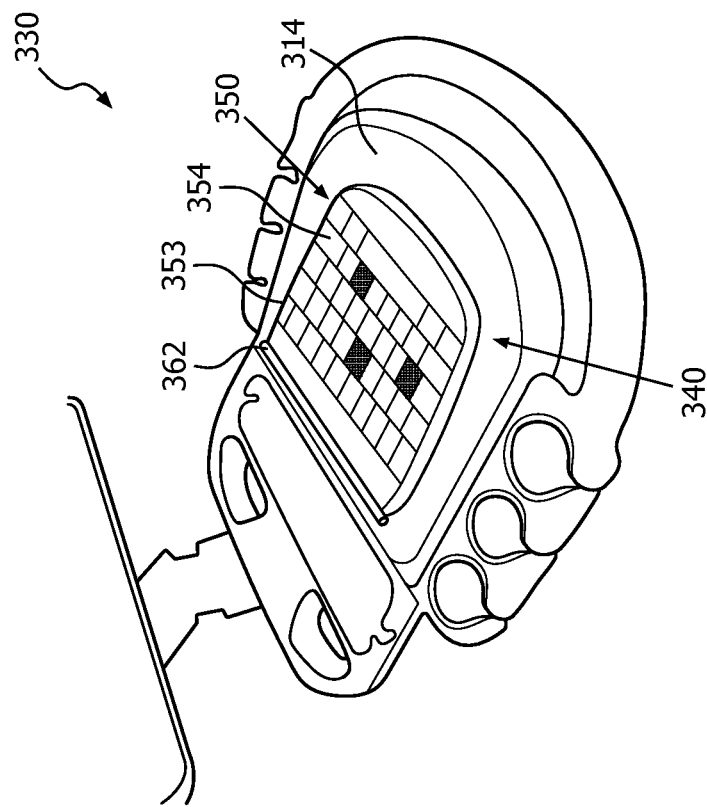
FIGS. 4A and 4B are simplified views of a control panel of an ultrasound imaging system illustrating a touch control panel movable between first and second positions.
Figure 4B:
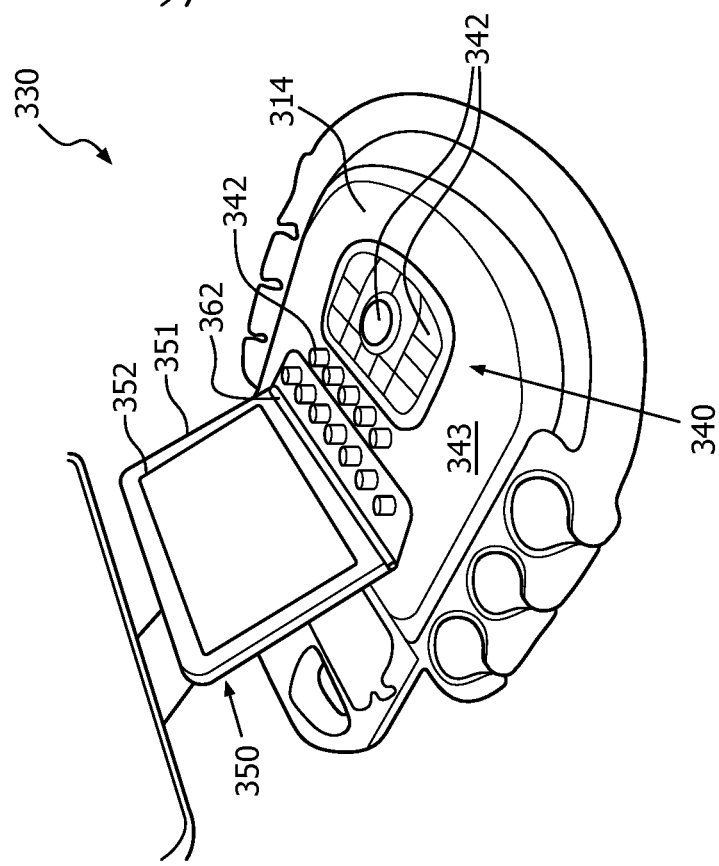

Referring now also to FIGS. 4A and 4B, additional features of ultrasound systems with a movable touch screen interface are described. FIGS. 4A and 4B show simplified views of a control platform 330 of an ultrasound system according to one embodiment of the present disclosure. The touch screen interface is configured to operate in a first mode when the touch control panel 350 is in a first position, e.g., an elevated position as illustrated in FIG. 4A, and is further configured to operate in a second mode when the touch control panel 350 is in a second position, e.g., a lowered position as illustrated in FIG. 4B. The touch control panel 350 is pivotably coupled to the control platform 314 via a hinge mechanism 362. The control platform 314 supports a manual control panel 340, which in this example is integrated into the control platform 314. A plurality of manual controls 342 is provided on the manual control panel 340. The touch control panel 350 in this embodiment includes two touch-sensitive displays (or simply touch displays). One or both of the touch displays may be capacitive displays. Any known or later developed touch-sensitive display technology may be used for implementing the touch displays 352 and 354. In some examples, the touch displays may be of equal size and/or sensitivity. In other examples, the touch displays may have a different size and one or more manual controls may also be provided on the touch control panel 350.

A first touch display 352 is located on one side 351 (e.g., forward side) of the touch control panel 350. The touch display 352 may span some or substantially all of a first major surface of the touch control panel 350. A second touch display 354 is provided on a second side 353 of the touch control panel 350 opposite the first side 351 (e.g., a rear side). The second touch display 354 may span some or substantially all of a second major surface of the touch control panel 350. Major surfaces refer generally to those surfaces of the touch control panel that have relatively larger surface area than other surfaces of the touch control panel. In further examples, the touch displays may be provided on surfaces other than the major surfaces. In yet further examples, the touch control panel 350 may include portions that are not touch-sensitive and/or include one or more manual controls in addition to any touch-sensitive controls implemented thereon.

In known systems, manual controls are typically provided on a surface which is generally horizontal or slightly downwardly inclined relative to the ground. Thus, when a user manipulates the manual controls of an ultrasound system, the user's hand may be generally horizontal or slightly upwardly angled, which position is also referred to as a resting or neutral hand position. Known ultrasound systems with fixed touch screen interfaces require the user's reach to extend and wrist angle increase in order to manipulate the touch screen interface, which hand position may be suboptimal from an ergonomics standpoint.

According to some examples herein, the touch control panel 350 is pivotable between a first position (e.g., an elevated position) and a second position (e.g., lowered position). The control platform 314, and particularly the support surface 343, may be generally horizontal or slightly downwardly inclined relative to the ground. In the elevated position, the touch control panel 350 may be angled relative to a support surface 343. The elevated position may thus also be referred to as angled or inclined position. In some examples, the angle between the lowered and elevated positions may be 5 degrees or more, 10 degrees or more, 25 degrees or more, 50 degrees or more, or 100 degrees or more. In some examples, the angle between the lowered and elevated positions may be anywhere from about 90 degrees to about 170 degrees. Different ranges of angles may be used in other examples as may be appropriate to achieve a desired ergonomic orientation of the touch control panel 350. When the touch control panel 350 is provided at the angled position, the reach and/or angle of the user's hand may be greater than an ergonomically preferred neutral hand position.

In the lowered position, the touch control panel 350 may be substantially parallel with the support surface 343. Thus, the touch control panel 350 may be generally horizontal or slightly downwardly inclined relative to the ground when the touch control panel 350 is in the lowered position. Typically, for ergonomics reasons, the support surface 343 may have a slight downward angle (i.e., native angle) and thus the touch control panel 350 may be provided at this native angle when in the lowered position. The lowered position may interchangeably be referred to as the zero-angle position or native-angle position. In the lowered position, the touch screen interface may be closer and at an ergonomically preferred angle allowing placement of the user's hand in an ergonomically preferred position (e.g., a resting or neutral position), for example when performing certain operations such as typing, annotation and sketching, and/or manipulation of 3D volumes. The control panel 330 may be configured to enable placement of the touch control panel 350 at any number of angled positions relative to the native angle of the control platform 314.

In the first position, the first touch display 352 is accessible to the user, while the second touch display 354 is generally inaccessible (or not easily accessible) as it is located on the side facing away from the user (e.g., the rear side). In the lowered position the first side 351 of the touch control panel 350 is brought near the manual control panel 340 facing the manual control panel 340. When the touch control panel 350 is in the lowered position, the second touch display 354 becomes accessible while the first touch display 352 is not accessible to the user. One or more of the manual controls 342 are also not accessible as they are located below the touch control panel 350 when the touch control panel is in this position. In the illustrated example, the touch control panel 350 covers all of the manual controls thus all of the manual controls become inaccessible in the second position. However, in other examples, one or more manual controls may be arranged on the manual control panel 340 such that they lie outside of the footprint of the touch control panel 350 and such that the user may be able to manipulate these one or more manual controls while operating the touch screen interface in the second mode.

The control panel 330 may be configured such that the inaccessible touch display is deactivated when switching between modes, e.g., to reduce consumption of power. That is, when the touch control panel 350 is provided in the elevated position, the first touch display 352 is activated while the second touch display 354 may be deactivated. When the touch control panel 350 is provided in the lowered position, the second touch display 354 is activated while the first touch display 352 may be deactivated. By deactivated it will be generally understood that power usage by a given display may be reduced for example by providing the given display in a stand-by mode, by dimming the display, or by powering down the display. Activating the display may include providing the display in active mode e.g., by powering up and/or illuminating the display.

Activating and deactivating of a respective display may occur automatically responsive to movement of the touch control panel 350 to one of the predetermined positions, e.g., responsive to an indication of position of the touch control panel 350. In this regards, the control panel 330 may include a position indicator (e.g., position indicator 366) configured to provide an indication of the position of the touch control panel 350 e.g., relative to the support surface 343. The position indicator 366 may be implemented using one or more position sensors, proximity sensors, or other known electromechanical devices capable of determining a relative position of the touch control panel 350. In some examples, the position indicator 366 may be incorporated in the hinge mechanism 362. In this manner, the hinge mechanism may be configured to provide an indication of the position of the touch control panel 350. In some examples, the position indicator (e.g., a proximity sensor) may be arranged operably on the support surface 343 and configured to detect placement of the touch control panel in proximity thereto (e.g., when the touch control panel is moved to the lowered position).

In some examples, the attachment mechanism 360 may be configured to limit movement of the touch control panel 350 between two or more predetermined positions (e.g., the lowered and elevated positions). For example, hinge mechanism 362 may include one or more position limiters 364 (e.g., first and second hard stops 364-1, 364-2). An upper hard stop 364-1 may be configured to limit rotation of the touch control panel 350 to a predetermined angular position. The hard stops 364-1 and 364-2 may be sufficiently robust to resist movement of the touch control panel 350 beyond the predetermined position, such as to maintain the touch control panel 350 in the predetermined position regardless of pressure applied to it during use of the touch screen interface. A lower hard stop 364-2, which may be similarly robust so as to resist movement of the touch control panel 350 beyond the limited lower position. In this manner, the hard stop 364-2 may prevent movement of the touch control panel 350 beyond the native-angle position, thereby reducing or eliminating contact between the first touch display 352 and the manual controls that may otherwise damage the display and/or controls. In some examples, a support member (not shown) may be provided on the support surface, alternatively or additionally, to the lower hard stop 364-2. The support member may be configured to support the touch control panel 350 in the native-angle position in a spaced arrangement with respect to the manual control panel 340 to prevent contact between the first touch display 352 and the manual controls 342 when the touch control panel 350 is in the lowered position.

In some examples, one or more of the hard stops 364-1, 364-2 may be adjustable. For example, the upper hard stop 364-1 may be configured to limit movement to two or more predetermined elevated positions, for example using a latch and release type mechanism. When the touch control panel is initially pivoted from the lowered position toward an elevated position, a latch mechanism may prevent movement beyond a first default elevated position. The hard stop may include a release which may enable the touch control panel to be pivoted beyond the first default elevated position to a second default elevated position. Any number of elevated positions may be provided. Similarly, the lower hard stop 364-2 may be configured to enable placement of the touch control panel 350 at two or more lowered positions, one of which may correspond with the native-angle position.

Figure 5:
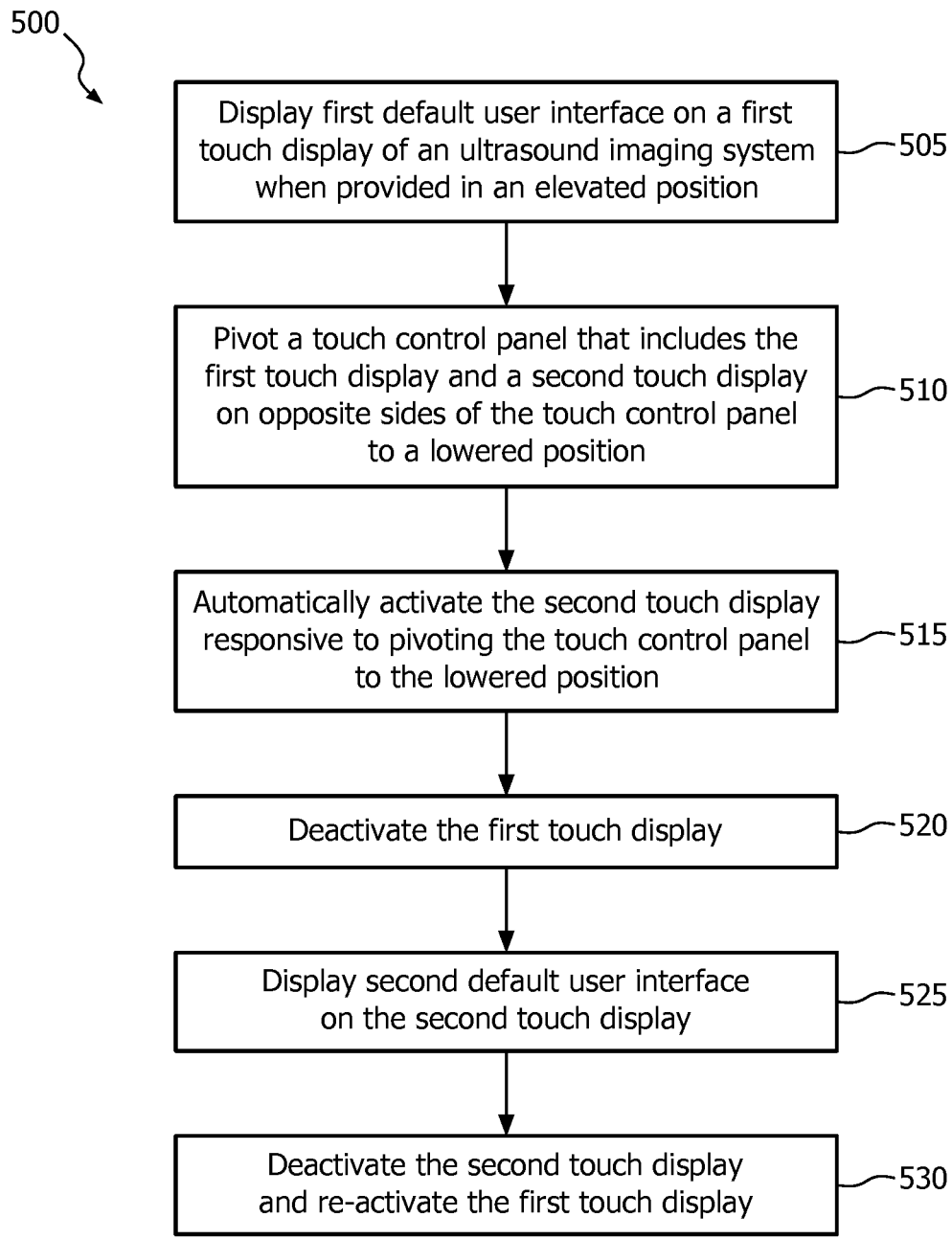
FIG. 5 is a flow diagram of one process which may be performed with ultrasound systems in accordance with the present disclosure.

Referring now also to FIGS. 5-8, additional aspects and methods of operation of ultrasound systems according to the present disclosure are described. FIG. 5 shows a flow diagram of a process 500 which may be performed using an ultrasound imaging system having a movable touch screen interface in accordance with some examples herein.

Initially, a touch control panel 350 of an ultrasound system may be positioned in a first position (e.g., elevated position) for operating the touch screen interface in a first mode. In this position, the first touch display 352 may be accessible and a first default user interface may be initially displayed on the touch display 352, as shown at block 505. In addition, one or more manual controls 342 may be accessible when operating the touch screen interface in the first mode. The first default user interface may therefore include secondary menus for performing functions that may be associated with operations generally controlled via the manual controls. For example, the first default user interface may include selection menus, or enable selection of clinically relevant measurements or other types of operations which may require minimal data entry or interaction with the touch screen interface. Menus or soft controls of the first default user interface may be presented via one or more touch-sensitive areas on the touch display 352 which may be associated with the first mode of operation of the ultrasound imaging system.

The touch display 352 may be moved, for example pivoted, to a second position relative to the manual control panel (e.g., a lowered position), as shown in block 510, which may switch the touch screen interface to a second mode. The ultrasound imaging system may be configured to automatically display a second default user interface 356 on the touch display 354 responsive to the moving of the touch display 352 to the second position. In some examples, the process may include sensing the position of the touch control panel 350 relative to the manual control panel 340, for example using a position indicator 366 of the attachment mechanism 360.

This second default user interface may be associated with a second mode of operation different from the first mode. Thus, the second default user interface may include interactive displays, menus or controls, which may be presented via one or more touch-sensitive areas associated with the second mode of operation. The second default user interface may include soft controls for functions that may be more suitably performed in a resting/neutral hand position. For example, extended interaction or manipulation of soft controls may be more suited for a resting/neutral hand position. Operations such as soft keyboard typing (see e.g., FIG. 4A), sketching and annotation (see e.g., FIG. 7A), and volume manipulation (see e.g., FIG. 7B) may typically require more extended interaction with the touch screen, for example as compared to making a menu selection, and may thus be more suited for a resting/neutral hand position. The second default user interface may present a touch screen interface (e.g., soft controls) which is different from the first default user interface. Additional default user interfaces may be provided at additional predetermined positions. The default user interfaces at the predetermined positions may be user-configurable. This may enable the user to select suitable soft controls for each of the default positions of the touch display as may be more suitable for any given clinical applications (e.g., diagnostic/pre-surgical cardiovascular and/or obstetrical applications, emergency/trauma applications, and others). For a given clinical application, the suitable soft controls may be selectable by either the user (e.g., purchaser of the ultrasound system or end users, such as the operator, sonographer, clinician) or the manufacturer to provide controls which are specific to (1) the imaging mode (e.g. 2D, color, Shear Wave, 3D imaging, etc.), (2) the tool set (e.g. labeled measurements, annotation, review, reporting, etc.), as well as to the clinical application. Within any clinical application, the user may have the flexibility to select specific soft controls for both the first and second touch displays for each imaging mode and associated tools, as may be needed.

As described, one or more of the touch displays may automatically activate or deactivate responsive to movement of the touch control panel between default positions. For example, the second touch display may be automatically activated responsive to pivoting of touch control panel to the lowered position, as shown in block 515. The touch display that is not positioned for use may be deactivated. For example, the first touch display 352 may be deactivated, as shown in block 520. This may occur automatically, e.g., responsive to pivoting of touch control panel to the lowered position. In some examples, both touch displays may remain active/illuminated even when inaccessible. Upon activation of the second touch display 354, a second default user interface may be provided on the second touch display 354, as shown at block 525. In a subsequent step, when the touch interface is switched again to the first mode (e.g., by pivoting the touch control panel to the elevated position), the second touch display 354 may be deactivated and the first touch display 352 may be automatically re-activated, as shown at block 530, responsive to pivoting of touch control panel to the elevated position.

As previously described, one or more of the first and/or second default user interfaces may be user-configurable to enable a user to tailor the touch screen interface as may be desired for a particular clinical use and/or application, as shown in FIG. 6. FIG. 6 illustrates two examples of clinically different ultrasound applications including an obstetric (OB) application and a cardiovascular (CV) application. In each clinical application, default user interfaces for each mode of operation of the touch screen interface may be further pre-set for 2D or 3D operations. As shown in the illustrated example, a user may be able to configure the ultrasound system to display desired default controls via the touch screen interface specific to: 1) clinical application (e.g., women's' health care or cardiac), 2) preset (e.g., OB general and TEE interventional), and 3) imaging mode (e.g., 2D imaging, frozen and 3D/4D imaging, live volume). The specific examples illustrated in FIG. 6 are provided for illustration only and do not limit the scope of the present disclosure. The default user interfaces to be displayed on the touch displays may be configurable for different combinations of clinical uses and/or applications, presets or modes than the ones illustrated. Also, it will be understood that, although a default user interface may be displayed when the touch screen interface is initially provided in one of the predetermined positions, the user is free to change the user interface on the touch screen as desired to perform any other functions besides those enabled by the default user interfaces. The default user interfaces provide an efficient and nearly effortless way of switching between common operations (e.g., operations that may be relevant to a particular clinical use or application) but do not otherwise limit the operability or use of the ultrasound system.

Figure 7B:
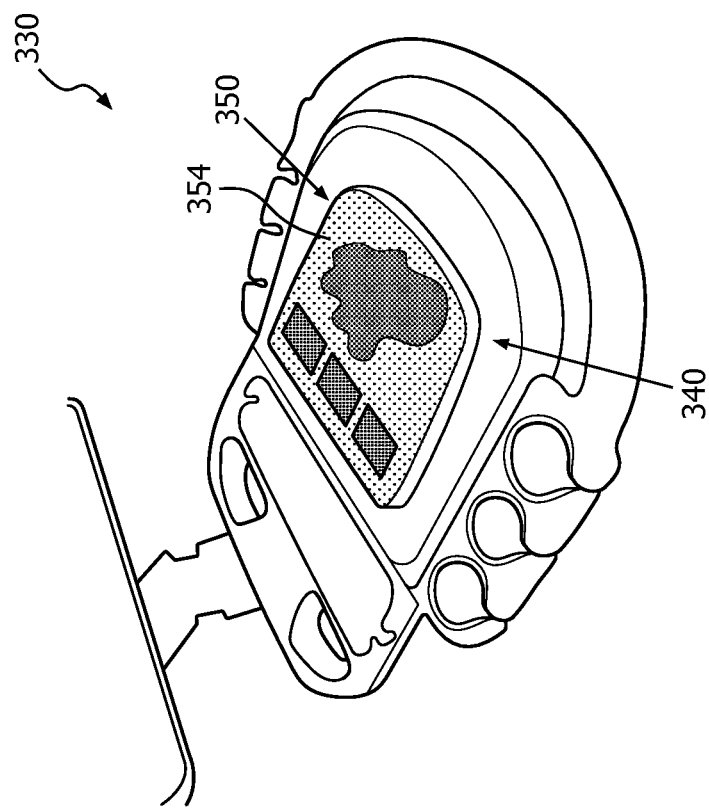
FIGS. 7A and 7B are simplified views of a control panel with a movable touch screen interface illustrated in one of a plurality of positions and illustrating example default user interfaces that may be provided in the illustrated position.
Figure 7A:
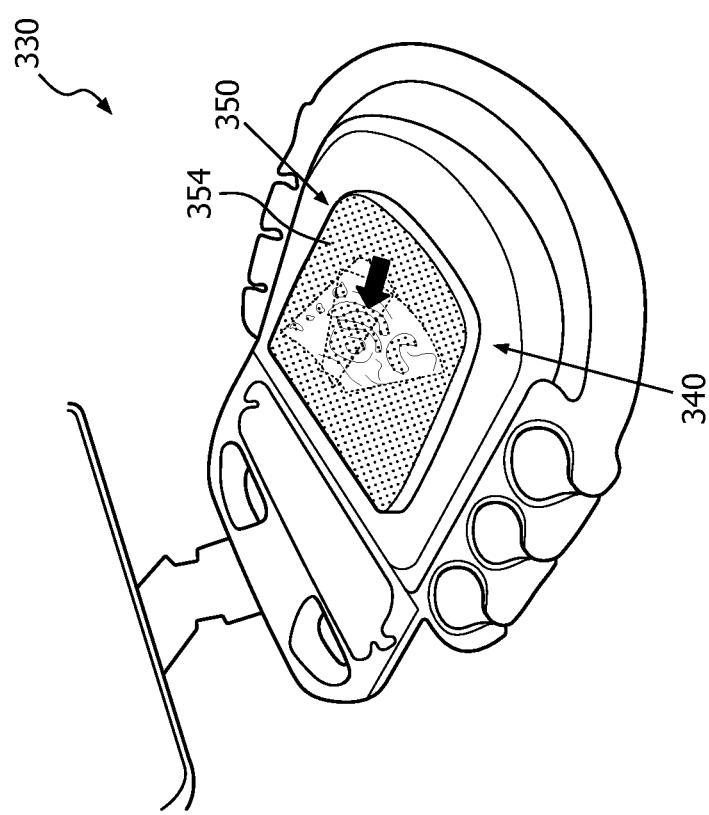

FIGS. 4B, and 7A-7B show simplified views of default user interfaces for the second mode (e.g., when the touch control panel is in the lowered position) according to some examples herein. In one example, the second default user interface may be configured to display a touch screen keyboard, e.g., as illustrated in FIG. 4B. In other examples, the second default user interface may be configured to display a mirror image of a captured image (e.g., a frozen 2D image), e.g., as illustrated in FIG. 7A. The second default user interface in this example may also display soft controls/tools for manipulating the image and/or obtaining clinically relevant information. The second default user interface may be configured to enable the user to annotate the image and/or perform erase, undo and other typical annotation and sketching functions. In a further example, the second default user interface may be configured to display an image of a 3D volume and enable the user to interact with the 3D volume, e.g., as illustrated in FIG. 7B. The second default user interface in this example may enable the user to zoom, rotate, pan, and crop the image as well as provide access to erase, undo and other functions that may be relevant to volume manipulation but which may not be otherwise accessible if the user is using the manual controls for volume manipulation.

The tools or applications that are associated with a particular user interface displayed on a touch display in a given mode may be independently and simultaneously executable from tools or applications that are associated with a user interface displayed on the touch display in another mode. That is, the user may be able to switch between tools or applications by simply switching the mode (e.g., by repositioning the touch display). This enables multiple workflows to be active during a given time. A current workflow in one mode of the touch screen interface may not need to be interrupted (e.g., ended) in order for the user to initiate or continue work on another workflow via another mode of the touch screen interface. Similarly, access to the manual controls is not prevented or disabled while the user is performing operations via the touch screen interface even when the touch control panel is in the lowered position. The user may temporarily move the touch control panel to the elevated position to access the manual controls below the touch screen panel. The workflow on the second touch display 354 may be temporarily suspended (e.g., paused) but need not be terminated while the user operates the manual controls. The user can return to the temporarily suspended workflow where left off without the need to reinitiate it (e.g., perform certain functions as may be appropriate at the start of a workflow) thereby improving operational efficiency.

Figure 8:
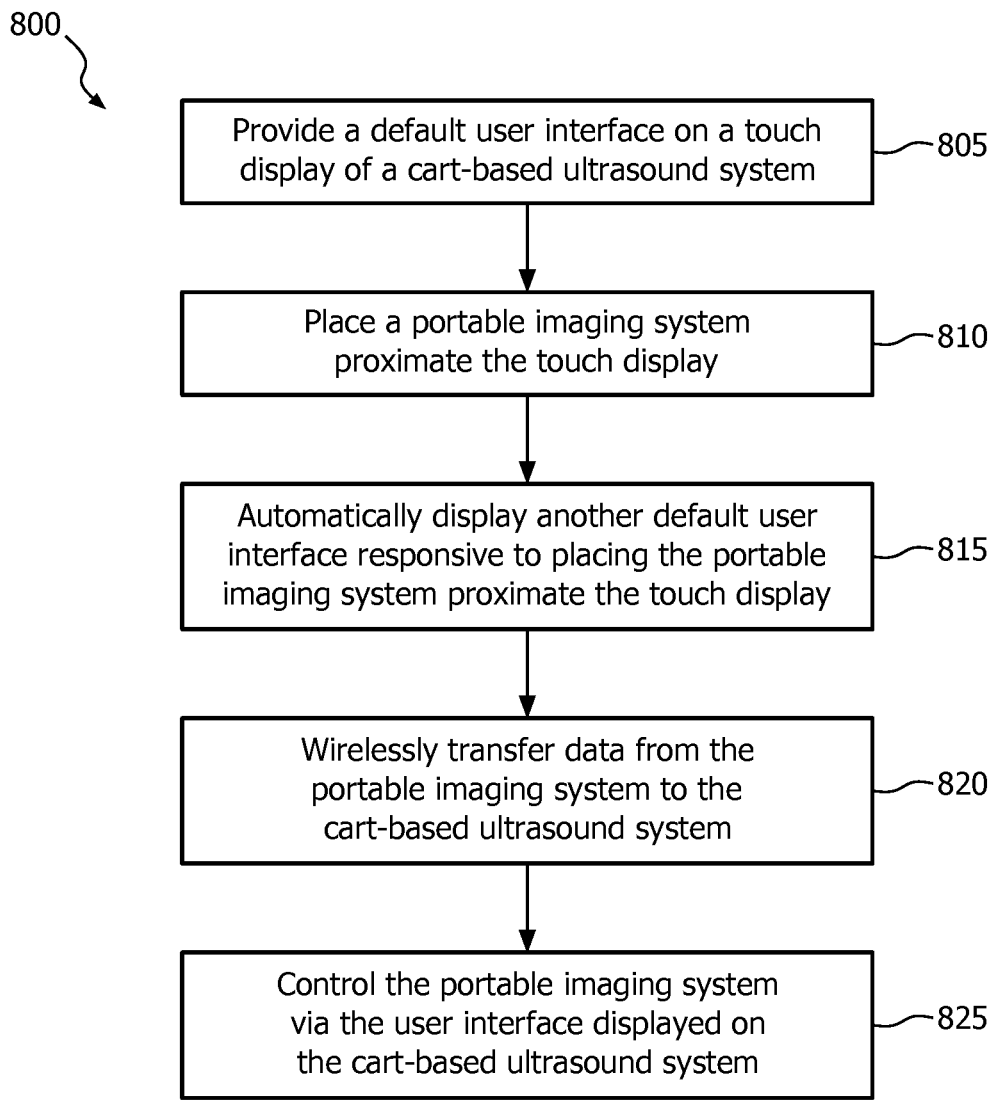
FIG. 8 is a flow diagram of another process which may be performed with ultrasound systems in accordance with the present disclosure.
Figure 9:
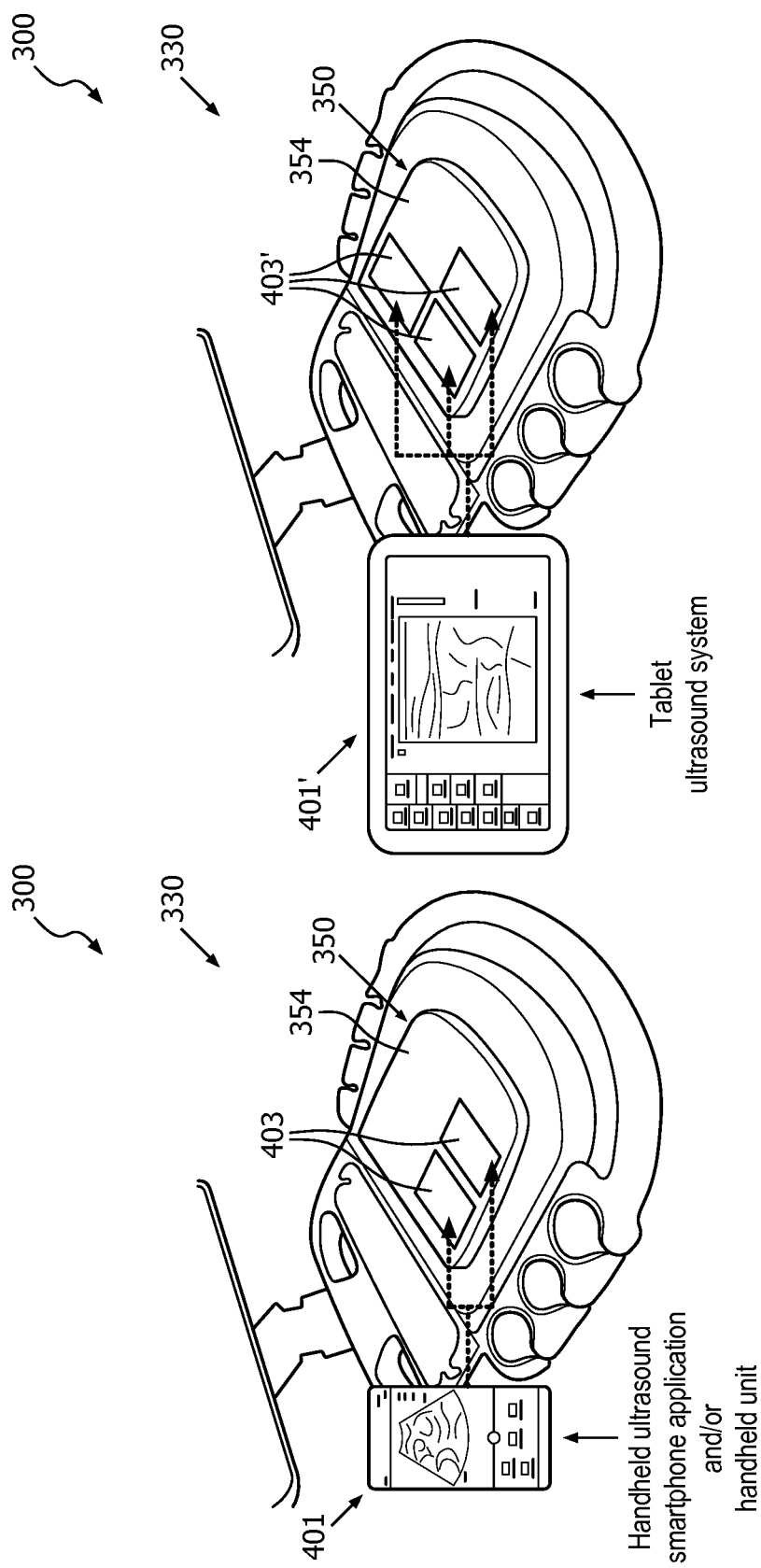
FIG. 9 is a simplified view of a control panel illustrating aspects of wireless data transfer via a multi-mode touch screen interface according to the present disclosure.

FIG. 8 shows a flow diagram of a process 800 which may be performed using an ultrasound imaging system having a movable touch screen interface in accordance with further examples herein. FIG. 9 shows a simplified view of a control panel illustrating aspects of wireless data transfer via a multi-mode touch screen interface according to the present disclosure.

Referring now also to FIGS. 8 and 9, data transfer operations may be more efficiently performed via a multi-mode touch screen interface according to the examples herein. More recently, portable imaging systems (e.g., mobile devices such as hand-held devices which execute ultrasound or other imaging applications) have been developed for example for use as part of emergency medicine and point-of-care treatment. With the introduction of such portable imaging systems into the healthcare environment, quick and easy transfer of data between imaging systems may be desirable, for example to transfer patient data and/or copies of ultrasound images and exams to a conventional cart-based ultrasound system for example at the point of transferring patient care to another department in the same hospital.

In an example process, a user interface may initially be provided on a touch display of a cart-based ultrasound system 300, as shown in block 805. A portable imaging system, such as a hand-held device (e.g., smartphone 401, tablet 401' in FIG. 9) configured to execute an application for ultrasound imaging, may be placed near the cart-based ultrasound system 300, as shown in block 810. By near or proximate it is generally meant within a range of typical wireless transfer communication protocols, such as Wi-Fi, Bluetooth, and the like. The portable imaging system (e.g., 401, 401') and the cart-based system (e.g., 300) may be equipped with one or more wireless communication devices, currently known or later developed, and the operable range may thus depend on the particular type of wireless technology used. Wireless communication between the portable imaging system and the cart-based ultrasound system may be automatically established when the portable imaging system is brought in proximity. In some examples, the portable imaging system may be placed in contact with the cart-based system, for example onto the touch display 354 such as when the touch display is provided in the lowered position.

A cart-based ultrasound system with multi-mode touch screen interface may be configured to automatically display another default user interface responsive to the placement of the portable imaging system in proximity, as shown in block 815 and also illustrated in FIG. 9. The default user interface displayed responsive to the proximity of the portable imaging system may include touch-sensitive portions (e.g., soft controls) configured for receiving user input associated with transferring data to and from the portable imaging system via the touch display of the cart-based ultrasound system. Data, including files, images, patient information, exam results, may then be wirelessly transferred from the portable imaging system to the cart-based system, as shown in block 820. Direct file/image transfer may thus be enabled in a manner which may be more expedient and user-friendly than conventional methods. One or more images (403, 403') received from the portable imaging system (401, 401') may be displayed on the touch display 354 and/or replicated on other displays such as additional monitors (e.g., monitor 216 of system 200). Various operations may be enabled via this "data transfer" interface, such as view and/or display incoming images from the portable imaging system, accept and assign destination for display and/or storage of incoming data (images, related patient/exam data), delete incoming images, project images, etc. In some examples, the portable imaging system may be controlled via the touch display 354 of the cart-based ultrasound system 300 while the portable imaging system remains in communicative mode and/or communication range of the ultrasound system 300. For example, displaying an image on or deleting an image from the portable imaging system may be performed responsive to user inputs received via the touch display 354.

In accordance with the present disclosure, a touch screen interface for a medical imaging system, such as an ultrasound system, may be implanted which may provide improved ergonomic access to frequently used controls as compared to existing medical imaging systems. By movably adjusting a distance and/or angle between the touch screen interface and the user in different modes of operation, the described system may improve the ergonomics and usability of the system without having to remove the manual controls or increase the overall size of the system. The examples herein may provide more intuitive methods for performing certain functions such as manipulating 3D volume data. The examples herein may provide more efficient and intuitive methods for transferring ultrasound images and data from mobile ultrasound applications and devices to cart-based ultrasound systems. The examples herein may provide means for supplementing existing ultrasound system design with additional functionality without increasing the size of the control panel and/or overall system footprint. The examples herein may provide better ergonomic access to frequently used tools or applications. The incorporation of a second mode for the touch screen interface may allow new mode-specific tools to be delivered to the user in a more intuitive and ergonomic manner without eliminating or displacing essential hard key controls. Data transfer between imaging systems may also be more intuitive and efficient in accordance with the present examples. This may be especially useful for hand-offs between Emergency/trauma personnel and other departments in a hospital setting.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this invention may be apparent to those skilled in the art upon studying the disclosure, or may be experienced by persons employing the novel system and method of the present invention. Another advantage of the present systems and method may be that conventional medical image systems can be easily upgraded to incorporate the features and advantages of the present systems, devices, and methods.

Examples in accordance with inventive aspects of the present disclosure are further described in the below enumerated paragraphs:

A1. An ultrasound imaging system comprising: a movable base; and a control panel supported by the movable base, the control panel including: a plurality of manual controls provided on a support surface; and a touch control panel movably coupled to the support surface, the touch control panel comprising a touch display configured to provide a touch-sensitive user interface, the touch control panel movable between a plurality of positions at each of which the touch display is at a different angle relative to the support surface, the touch display configured to automatically change a user interface provided on the touch display responsive to movement of the touch display to any of the plurality of positions.

A2. The ultrasound imaging system according to paragraph A1, wherein the touch control panel is movable relative to the plurality of manual controls between a first position in which one or more of the plurality of manual controls are accessible and a second position in which the one or more of the plurality of manual controls are not accessible.

A3. The ultrasound imaging system according to any of paragraphs A1 or A2, wherein the touch display is a first touch display provided on a first side of the touch control panel, the touch control panel further comprising a second touch display provided on a second side of the touch control panel opposite the first side, and wherein the touch control panel is pivotable between a first position and a second position, the first position corresponding to an elevated position in which the first touch display is accessible and the second position corresponding to a lowered position in which the second touch display is accessible.

A4. The ultrasound imaging system according to paragraph A3, wherein the elevated position is a first elevated position and wherein the touch control panel is further pivotable to a second elevated position in which the first touch display is accessible.

A5. The ultrasound imaging system according to any of paragraphs A3 or A4, wherein the ultrasound system is configured to automatically activate the second touch display responsive to pivoting of the touch control panel to the lowered position.

A6. The ultrasound imaging system according to any of paragraphs A3-A5, wherein the ultrasound system is further configured to deactivate the first touch display when the touch panel is pivoted to the lowered position.

A7. The ultrasound imaging system according to any of paragraphs A3-A6, wherein the touch control panel is coupled to the support surface via a hinge mechanism configured to provide an indication of a position of the touch control panel.

A8. The ultrasound imaging system according to paragraph A7, wherein the hinge mechanism comprises a position limiter configured to limit rotation of the touch control to within a predetermined range.

A9. The ultrasound imaging system according to any of paragraphs A3-A8, wherein the first touch display, the second touch display, or both are capacitive displays.

A10. The ultrasound imaging system according to any of paragraphs A1-A9, wherein control panel is separable from the movable base.

A11. The ultrasound imaging system according to any of paragraphs A1-A10 further comprising a monitor separate from the touch control panel.

A12. The ultrasound imaging system according to paragraph A11, wherein the monitor is connected to the movable base via an articulating arm.

A13. The ultrasound imaging system according to any of paragraphs A1-A12 further comprising at least one transducer probe removably coupled to the movable base.

B1. An ultrasound imaging system comprising: a movable base; a control panel supported by the movable base, the control panel including: a support surface; and a touch control panel movably coupled to the support surface, the touch control panel comprising a first touch display on a first side of the touch control panel and a second touch display on a second side of the touch control panel opposite the first side, the touch control panel pivotable between a first position at which the touch control panel is at a first angle relative to the support surface and a second position in which the touch control panel is at a second angle relative to the support surface smaller than the first angle, the first and second touch displays configured to provide respective first and second user interfaces responsive to pivoting of the touch control panel to the first and second position, respectively.

B2. The ultrasound imaging system according to paragraph B1, wherein the first position may correspond to an elevated position in which the first touch display is accessible and the second position corresponds to a lowered position in which the second touch display is accessible.

B3. The ultrasound imaging system according to any of paragraphs B1 and B2, wherein the first touch display is inaccessible in the lowered position.

B4. The ultrasound imaging system according to any of paragraphs B1-B3 further comprising a transducer probe removably coupled to the base.

C1. A method of operating an ultrasound imaging system, comprising: displaying a first default user interface on a touch display of an ultrasound imaging system when the touch display is in a first position relative to a manual control panel of the ultrasound imaging system, wherein the first default user interface includes one or more touch-sensitive areas on the touch display associated with a first mode of operation; moving the touch display to a second position relative to the manual control panel; automatically displaying a second default user interface on the touch display responsive to the moving the touch display to the second position, the second default user interface associated with a second mode of operation different from the first mode.

C2. The method according to paragraph C1, wherein the manual control panel comprises a plurality of manual controls, wherein the touch display is part of a touch control panel, and wherein moving the touch display comprising moving the touch control panel from the first position in which the plurality of manual controls is accessible to the second position in which the plurality of manual controls is inaccessible.

C3. The method according to any of paragraphs C1 or C2, wherein the touch display is a first touch display located on a first side of a touch control panel, the touch control panel further comprising a second display located on a second side of the touch control panel opposite the first side, and wherein moving the touch display comprises pivoting the touch control panel relative to the manual control panel from the first position in which the first touch display is accessible to the second position in which the second touch display is accessible.

C4. The method according to paragraph C3 further comprising automatically activating the second touch display responsive to said pivoting the touch control panel from the first position to the second position.

C5. The method according to any of paragraphs C3 or C4 further comprising deactivating the first touch display responsive to said pivoting the touch control panel from the first position to the second position.

C6. The method according to any of paragraphs C1-C5, wherein the touch display is part of a touch control panel, the method further comprising sensing a position of the touch control panel relative to the manual control panel.

C7. The method according to any of paragraphs C1-C6 further comprising: placing a portable imaging system proximate the touch display; and wirelessly transferring data from the portable imaging system to the ultrasound imaging system.

C8. The method according to paragraph C7 further comprising automatically providing a third default user interface on the touch display responsive to placing a portable imaging system proximate the touch display, the third default user interface comprising touch-sensitive portions configured for receiving user input associated with transferring data to and from the portable imaging system.

C9. The method according to any of paragraphs C7 or C8, wherein the placing a portable imaging system proximate the touch display comprises placing the portable imaging system onto the touch display.

C10. The method according to any of paragraphs C7-C9 further comprising deleting an image from the portable imaging system or controlling a display of the image on the portable imaging system responsive to user inputs received via the second touch display.

C11. The method according to any of paragraphs C1-C10 further comprising pausing a first workflow on the touch display responsive to movement of the touch display from one of the first and second positions to the other one of the first and second positions; reactivating the first workflow responsive to movement of the touch display to the one of the first and second positions.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
a movable base; and
a control panel irremovably coupled to the movable base, the control panel including:
a plurality of manual controls integrated into a support surface of the control panel; and
a touch control panel pivotally coupled to the support surface, the touch control panel comprising a first touch display on a first side of the touch control panel and a second touch display on a second side of the touch control panel opposite the first side,
wherein the touch control panel is configured to automatically deactivate the second touch display, and to automatically provide a first touch-sensitive user interface on only the first touch display when the touch control panel is pivoted from a lowered position, in which the touch control panel is positioned over the plurality of manual controls and the plurality of manual controls are physically not accessible, to an elevated position, in which the plurality of manual controls are accessible, and
wherein the touch control panel is configured to automatically deactivate the first touch-display, and to automatically provide a second touch-sensitive user interface different from the first touch-sensitive user interface on the second touch display, when the touch control panel is pivoted from the elevated position to the lowered position.

2. The ultrasound imaging system of claim 1, wherein the second touch-sensitive user interface does not include one or more first touch-controls provided on the first touch-sensitive user interface, and wherein the first touch-sensitive user interface does not include one or more second touch-controls provided on the second touch-sensitive user interface.

3. The ultrasound imaging system of claim 1, wherein the touch control panel is coupled to the support surface via a hinge mechanism configured to provide an indication of a position of the touch control panel.

4. The ultrasound imaging system of claim 3, wherein the hinge mechanism comprises a position limiter configured to limit rotation of the touch control to within a predetermined range.

5. The system of claim 4, wherein the predetermined range is adjustable.

6. The system of claim 4, wherein the position limiter is configured to latch the touch screen in the first position.

7. The ultrasound imaging system of claim 1, wherein the first touch display, the second touch display, or both are capacitive touch displays.

8. The ultrasound imaging system of claim 1 further comprising a monitor separate from the touch control panel.

9. The ultrasound imaging system of claim 8, wherein the monitor is connected to the movable base via an articulating arm.

10. The system of claim 1, wherein the touch control panel automatically displays a touch keyboard when pivoted to the second position.

11. A method of operating an ultrasound imaging system, the method comprising:
providing an ultrasound system comprising a movable base and a control panel irremovably coupled to the movable base, wherein the control panel includes a plurality of manual controls integrated into a support surface thereof, and a touch control panel is pivotally coupled to the support surface and comprises a first touch display on a first side of the touch control panel and a second touch display on a second side of the touch control panel opposite the first side;
deactivating the second touch display and displaying one or more first user controls only on the first touch display of the touch control panel, wherein said deactivating and displaying are automatic responsive to a determination that the touch control panel is in an elevated position relative to the manual control panel in which the manual controls are physically accessible;
sensing a position of the touch control panel relative to the manual control panel after the touch control panel is pivoted to determine whether the touch control panel has been pivoted to a lowered position in which the one or more of the manual controls are physically inaccessible; and
displaying one or more second user controls different from the first user controls on a second touch display of the touch control panel located on a side of the touch control panel opposite the first touch display, wherein said displaying is automatic responsive to a determination that the touch control panel has been pivoted to the lowered position.

12. The method of claim 11, further comprising at least one of:
automatically activating the second touch display responsive to said pivoting the touch control panel from the first position to the second position; and
deactivating the first touch display responsive to said pivoting the touch control panel from the first position to the second position.

13. The method of claim 11, further comprising:
placing a portable imaging system proximate the touch control panel; and
wirelessly transferring data from the portable imaging system to the ultrasound imaging system.

14. The method of claim 11, further comprising automatically providing a third default user interface on an active one of the first and second touch displays responsive to placing a portable imaging system proximate the touch control panel, the third default user interface comprising touch-sensitive portions configured for receiving user input associated with transferring data to and from the portable imaging system.

15. The method of claim 14, wherein the placing a portable imaging system proximate the touch control panel comprises placing the portable imaging system onto the touch control panel.

16. The method of claim 14, further comprising deleting an image from the portable imaging system or controlling a display of the image on the portable imaging system responsive to user inputs received via the second touch display.

\* \* \* \* \*